United States Patent [19] [11] 4,008,312
Annen et al. [45] Feb. 15, 1977

[54] PREGNANE-21-OIC ACID DERIVATIVES

[75] Inventors: Klaus Annen; Helmut Hofmeister; Henry Laurent; Klaus Kieslich; Hans Wendt; Klaus Peter Mengel, all of Berlin, Germany

[73] Assignee: Schering Aktiengesellschaft, Berlin & Bergkamen, Germany

[22] Filed: Oct. 29, 1975

[21] Appl. No.: 626,775

[30] Foreign Application Priority Data

Oct. 31, 1974 Germany ............................ 2451971

[52] U.S. Cl. ........................ 424/241; 260/239.55 D
[51] Int. Cl.² ........................ A61K 31/58; C07J 1/00
[58] Field of Search ................ 260/397.1, 239.55 D; /Machine Searched Steroids

[56] References Cited
UNITED STATES PATENTS 3,906,095 9/1975 Laurent et al. ................ 260/397.1

Primary Examiner—Elbert L. Roberts
Attorney, Agent, or Firm—Millen & White

[57] ABSTRACT

Pregnane-21-oic acid derivatives of the formula

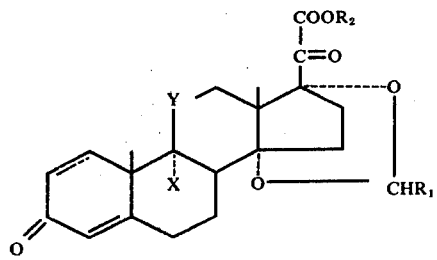

wherein
the linkage ═══ represents a single bond or a double bond;
X is hydrogen, fluorine or chlorine;
Y is methylene, hydroxymethylene, alkanoyloxymethylene, carbonyl, fluoromethylene or chloromethylene;
$R_1$ is hydrogen, alkyl of 1–6 carbon atoms, phenyl or naphthyl substituted with 0–3 lower alkyl, lower alkoxy or chlorine; and
$R_2$ represents a hydrogen atom, the cation of a physiologically compatible base or the residue of a physiologically acceptable alcohol of 1–18 carbon atoms.

These compounds exhibit useful antiinflammatory activity when topically applied to inflamed skin.

20 Claims, No Drawings

PREGNANE-21-OIC ACID DERIVATIVES

BACKGROUND OF THE INVENTION

This invention relates to pharmacologically active pregnane-21-oic acid derivatives, to processes for the preparation and use thereof and to medicinal agents containing these pregnane-21-oic acid derivatives.

DOS (German Unexamined Laid-Open Application) 2,204,361 discloses 20-oxopregnane-21-oic acid derivatives which differ essentially from the pregnane-21-oic acid derivatives of the present invention in that they have no substituents in the 14α- and 17α- positions. This DOS describes the possibility of producing the previously known pregnanoic acid derivatives from the corresponding 20-hydroxypregnene-21-oic acid derivatives by oxidizing the latter in an inert solvent with oxidizing heavy metal oxides, such as manganese(IV) oxide or lead(IV) oxide. It can be seen from the specification and examples of DOS 2,204,361 that it is unnecessary to observe critical specific reaction conditions when carrying out the oxidation method described in this reference.

OBJECTS OF THE INVENTION

It is a general object of this invention to provide novel pregnane-21-oic acid derivatives having substantial antiinflammatory activity upon topical administration, and methods for the preparation and use thereof.

Another object of this invention is to provide pharmaceutical compositions containing novel pregnane-21-oic acid derivatives as an antiinflammatory agent.

A further object of this invention is to provide an improved method for treating inflammatory skin diseases.

Upon study of the specification and appended claims, further objects and advantages of this invention will become apparent to those skilled in the art.

SUMMARY OF THE INVENTION

Briefly, the above and other objects, features and advantages of the present invention are attained in one aspect thereof by providing pregnane-21-oic acid derivatives of the formula

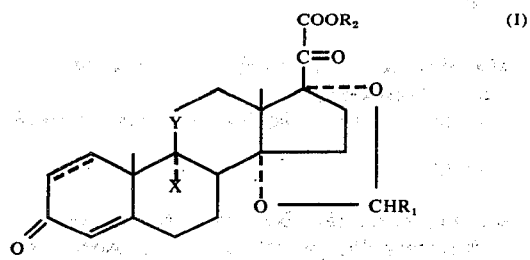

wherein
the linkage ---- represents a single bond or a double bond;
X is hydrogen, fluorine or chlorine;
Y is methylene, hydroxymethylene, alkanoyloxymethylene, carbonyl, fluoromethylene or chloromethylene;
$R_1$ is hydrogen, alkyl of 1-6 carbon atoms, phenyl or naphthyl substituted with 0-3 lower alkyl, lower alkoxy or chlorine; and
$R_2$ represents a hydrogen atom, the cation of a physiologically compatible base or the residue of a physiologically acceptable alcohol of 1-18 carbon atoms.

DETAILED DISCUSSION

In the compounds of Formula I, the alkanoyloxymethylene group Y is preferably derived from an n-alkanecarboxylic acid of 1-8 carbon atoms, e.g. formic acid, acetic acid, propionic acid, butyric acid, caproic acid, etc.

The cation of a physiologically compatible base $R_2$ is any suitable carboxylic acid salt cation, e.g. the sodium, potassium or ammonium cation.

The residue of a physiologically acceptable alcohol $R_2$ is an optionally substituted hydrocarbon residue of 1-18, preferably 1-12, carbon atoms which can be aliphatic or cycloaliphatic, saturated or unsaturated, substituted or unsubstituted.

Illustrative substituents on the group $R_2$ are, for example: lower alkyl groups, e.g. methyl, ethyl, propyl, isopropyl, butyl or tert.-butyl; aryl groups, e.g. phenyl, cyclopentyl or cyclohexyl; hydroxy groups; lower alkoxy groups, e.g. methoxy, ethoxy, propoxy, butoxy or tert.-butoxy; a free or esterified carboxyl group and the sodium and potassium salts thereof; amino groups and the salts thereof; mono- or di-lower alkylamino groups, e.g. methylamino, dimethylamino, ethylamino, diethylamino, propylamino or butylamino and the salts thereof; etc. Preferred salts of the amino, mono-lower alkylamino or di-lower alkylamino groups are the hydrochlorides, hydrobromides, sulfates, phosphates, oxalates, maleates or tartrates of these groups.

Illustrative groups $R_2$ include but are not limited to: methyl, carboxymethyl, ethyl, 2-hydroxyethyl, 2-methoxyethyl, 2-aminoethyl, 2-dimethylaminoethyl, 2-carboxyethyl, propyl, allyl, cyclopropylmethyl, isopropyl, 3-hydroxypropyl, propynyl, 3-aminopropyl, butyl, sec.-butyl, tert.-butyl, 2-butyl, cyclobutyl, pentyl, isopentyl, tert.-pentyl, 2-methylbutyl, cyclopentyl, hexyl, cyclohexyl, cyclohex-2-enyl, cyclopentylmethyl, heptyl, benzyl, 2-phenylethyl, octyl, bornyl, isobornyl, menthyl, nonyl, decyl, 3-phenylpropyl, 3-phenylprop-2-enyl, dodecyl, tetradecyl, hexadecyl and octadecyl.

The substituent $R_1$ is hydrogen, an alkyl group of 1-6 carbon atoms or an optionally substituted phenyl or naphthyl group. Suitable substituents of the phenyl or naphthyl group are, for example: lower alkyl groups, such as the methyl group; lower alkoxy groups, such as the methoxy group; or halogen atoms, such as the fluorine atom or the chlorine atom. Suitable substituents $R_1$ include but are not limited to: methyl, ethyl, propyl, butyl, phenyl, o-, m- or p-tolyl, o-, m- or p-methoxyphenyl, o-, m- or p-fluorophenyl, o-, m- or p-chlorophenyl, α- or B-naphthyl.

Especially preferred are those pregnane-21-oic acid derivatives of general Formula I meeting one or more of the following criteria:

a. X is hydrogen and Y is methylene, α- or β-hydroxymethylene, carbonyl or β-fluoromethylene;

b. X is fluorine and Y is β-hydroxymethylene or carbonyl;

c. X is chlorine and Y is β-hydroxymethylene, carbonyl, β-fluoromethylene group or a β-chloromethylene group;

d. Compounds wherein $R_1$ is alkyl of 1-6 carbon atoms;

e. Compounds wherein $R_1$ is phenyl or naphthyl substituted by 0–3, preferably 0–1, of lower alkyl, lower alkoxy or halogen, especially methyl, methoxy, fluorine or chlorine;
f. Compounds wherein $R_2$ is alkyl of 1–6 carbon atoms;
g. Compounds wherein $R_2$ is cycloaliphatic or aromatic with 5 or 6 ring carbon atoms;
h. Compounds wherein $R_2$ is hydrogen;
i. Compounds wherein $R_2$ is sodium;

Several suitable process are available for the preparation of the novel pregnane-21-oic acid derivatives of general Formula I, e.g. according to variations (a) through (f) set forth below:

a. a compound of general Formula II

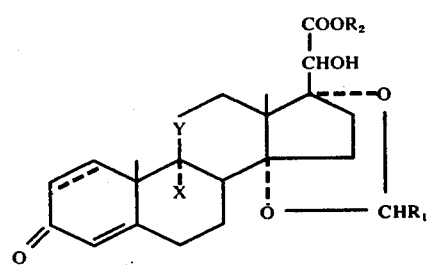

wherein ----, X, Y, $R_1$ and $R_2$ have the above-indicated values,
is oxidized with oxidizing heavy metal oxides;

b. a compound of general Formula III or the hydrate or acetal of these aldehydes

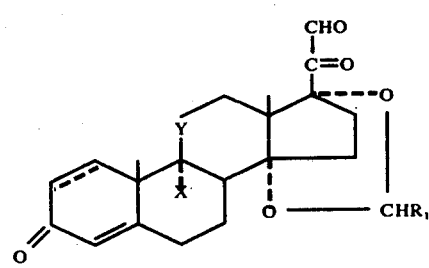

wherein --- X, Y and $R_1$ have the same meanings as indicated in Formula I,
is oxidized in the presence of an alcohol with oxidizing heavy metal oxides or with atmospheric oxygen; or c. for preparing $\Delta^{1,4}$-pregnadiene-21-oic acid derivatives of general Formula I, the compounds of general Formula I saturated in the 1,2-position are dehydrogenated; or d. for preparing pregnane-21-oic acid derivatives of general Formula I wherein Y is a β-hydroxymethylene group and X is a fluorine or chlorine atom, an epoxide of general Formula IV

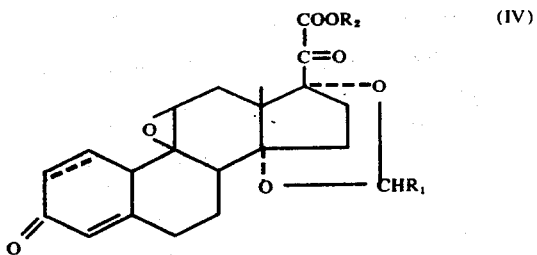

wherein ----, $R_1$ and $R_2$ have the same meanings as in Formula I,
is ring opened with hydrogen chloride or hydrogen fluoride; or e. for preparing pregnane-21-oic acid derivatives of general Formula I in which Y is a chlorine atom, hypochlorous acid, chlorine, or fluorine and chlorine are chemically added to a compound of general Formula V

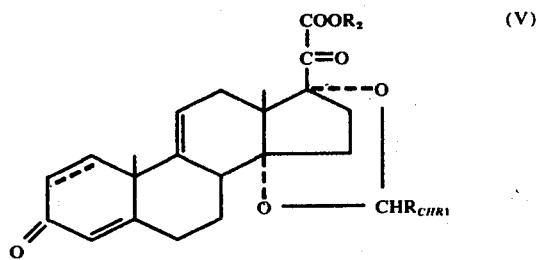

wherein ---- $R_1$ and $R_2$ have the same meanings as in Formula I; or f. a compound of general Formula VI

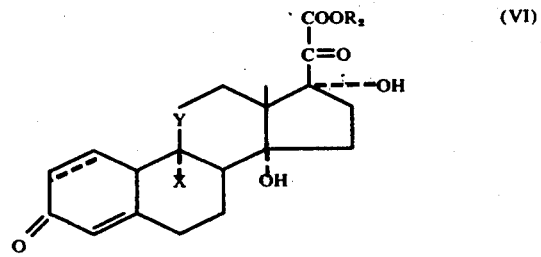

wherein ---- X, Y and $R_2$ have the same meanings as in Formula I,
is acetalized with an aldehyde of general Formula VII $$R_1CHO \qquad (VII)$$

wherein $R_1$ has the above-indicated values.

A hydroxy group present in the 11-position is optionally oxidized to the keto group; the esters of general Formula I are optionally reacted in the presence of basic catalysts with the finally desired alcohol; or these esters are saponified and, if desired, reesterified.

The novel pregnane-21-oic acid derivatives of general Formula I can also be prepared from the corresponding 20-hydroxy compounds of general Formula II by oxidizing the latter, according to process variation (a), in an inert solvent with oxidizing heavy metal oxides, e.g. manganese(IV) oxide or lead(IV) oxide. However, when conducting this reaction, it is necessary to make sure, by exerting an exact control over the reaction conditions, that only the quantity of oxidizing agent required for the reaction is being consumed, since the thus-formed pregnane-21-oic acid derivatives of general Formula I are, in contrast to the known pregnanoic acid derivatives, in most cases of low stability under the reaction conditions utilized and are very readily split oxidatively.

The process of this invention according to variant (a) can be effected in those inert solvents customarily used in oxidation reactions in steroid chemistry. Suitable solvents are well known in the art and include but are not limited to: hydrocarbons such as cyclohexane, benzene, toluene or xylene; chlorinated hydrocarbons such as methylene chloride, chloroform, carbon tetrachloride, tetrachloroethylene or chlorobenzene; ketones such as acetone, methyl ethyl ketone, methyl isobutyl ketone or acetophenone; preferably ethers, such as diethyl ether, diisopropyl ether, dibutyl ether, tetrahydrofuran, dioxane or glycol dimethyl ether; and/or alcohols, such as methanol, ethanol, isopropanol or tert.-butanol. The process of this invention can also be conducted in mixtures of the abovementioned solvents.

The process of this invention according to variation (a) can be accomplished, for example, with the use of manganese(IV) oxide or lead(IV) oxide. Preferred for this variation is the use of active manganese(IV) oxide, as is customary in steroid chemistry for oxidation reactions.

The reaction according to modification (a) preferably takes place at a reaction temperature of between 0° and 50° C.

To ensure that only the amount of manganese(IV) oxide or lead(IV) oxide required for the oxidation is being consumed, it is advantageous in a preliminary experiment to withdraw aliquots from the reaction mixture at time intervals, to examine these samples analytically, e.g. by thin-layer chromatography, and thus to determine the optimum reaction time. The latter is very much dependent on the structure of the 20-hydroxy compounds used in the reaction; normally, the reaction time is 5–30 minutes when the reaction is conducted at room temperature.

On the other hand, it is also possible to determine by means of preliminary experiments how much lead(IV) oxide or active manganese(IV) oxide is required for the oxidation.

The starting material for process variation (a) can be prepared from the corresponding 21-hydroxy-20-oxopregnane derivatives. For this purpose, the latter are dissolved in an alcohol, the solution is combined with copper(II) acetate and the mixture is agitated for several days at room temperature. The mixture is then combined with aqueous ammonia, extracted for example with methylene chloride; the organic phase is then washed with water, dried and concentrated under vacuum. A crude product is thus obtained consisting of a mixture of the 20α- and 20β-hydroxy steroids. This mixture can be separated by chromatography or fractional crystallization, or it can be used without any further purification as the starting material for the process of this invention according to variation (a).

It is theoretically possible to prepare the pregnane-21-oic acid derivatives of general Formula I from compounds of general Formula III by reacting these compounds in an alcohol with an amount of an oxidizing heavy metal salt stoichiometrically required for the reaction, e.g. silver oxide, lead(IV) oxide, minium, vanadium(V) oxide or active manganese(IV) oxide; however, the yields of the desired product obtained in this reaction are normally unsatisfactory. Surprisingly, higher yields of the products are obtained by oxidizing the compounds of general Formula III, or the hydrates or hemiacetals thereof, in an alcohol containing a catalytic amount of cyanide ions buffered to pH 4–7, with atmospheric oxygen or active manganese(IV) oxide.

The yields can be additionally improved by conducting the oxidation under the aforementioned conditions in the presence of dipolar aprotic solvents.

This preferred embodiment of process variation (b) can be accomplished, for example, as follows:

Atmospheric oxygen or active manganese(IV) oxide, as customarily employed for oxidation reactions, is utilized for this variation of the process; see L. F. Fieser and M. Fieser, Reagents for Organic Synthesis, John Wiley and Sons, Inc., New York, London, Sydney: 637 et seq. (1967).

For this process variation, the alcohols preferably employed are primary or secondary aliphatic, cycloaliphatic or aryl alcohols of 1–12 carbon atoms, e.g. methanol, ethanol, propanol, hexanol, cyclohexanol, isopropanol, butanol, butan-2-ol, pentanol, octanol, benzyl alcohol, etc.

This reaction is conducted with the use of cyanide ions as the catalyst. Reagents yielding cyanide ions are preferably alkali cyanides, e.g. sodium or potassium cyanide. Preferably, 0.01 mole to 10 moles and especially 0.1–1.0 mole of cyanide is utilized per mole of compound III. If alkali cyanides are used as the cyanide ion yield reagents, the reaction is conducted by furthermore adding to the reaction mixture the amount of mineral acids, e.g. sulfuric acid, phosphoric acid or hydrogen chloride; sulfonic acids, e.g. p-toluenesulfonic acid; or carboxylic acids, e.g. formic acid or acetic acid, sufficient to buffer the alkali cyanide to give a pH of 4–7, preferably 4–6, in the reaction mixture.

This reaction is preferably conducted in the presence of dipolar aprotic solvents. Suitable dipolar aprotic solvents are known in the art and include but are not limited to: dimethylformamide, N-methylacetamide, dimethylacetamide, N-methylpyrrolidone, dimethyl sulfoxide, sulfolane, dimethylsulfone, hexamethylphosphoric triamide, n-alkyl cyanides of 1–5 carbon atoms in the alkyl residue such as acetonitrile, etc.

The reaction is suitably conducted by utilizing as the solvent, per gram of compound III, 2 ml.–200 ml. of a mixture consisting of 5–50%, preferably 10–30% (by volume), lower alcohol and correspondingly 95–50%, preferably 30–90%, dipolar aprotic solvent.

The process is suitably accomplished at a reaction temperature of between −20° C. and +100° C. and preferably at a reaction temperature of 0°–50° C. The reaction time is dependent on the reaction temperature and the selection of reactants; in general, the reaction time is 5–120 minutes with the use of atmospheric oxygen and 1–30 minutes with the use of active manganese(IV) oxide.

The starting compounds of general Formula III can be produced as is conventional, e.g. by reacting the corresponding 21-hydroxy steroids for 20–120 minutes with copper(II) acetate and atmospheric oxygen in a lower primary alcohol of 1–4 carbon atoms at room temperature. During this reaction, mixtures of the free aldehydes and their hemiacetals are obtained which can be used without further purification as the starting materials for the process of the present invention.

The process of this invention according to process variations (c), (d) and (e), as well as the optionally conducted subsequent reactions can be effected, for example, under the conditions as described in DOS 2,264,003.

The process of this invention in accordance with process variation (f) can be accomplished, for example, under the conditions described in DOS 1,929,429.

The novel pregnane-21-oic acid derivatives of general Formula I are pharmacologically active substances distinguished, in particular, by possessing, upon topical administration, a pronounced anti-inflammatory effectiveness, whereas they are practically inactive systemically. Moreover, these pregnane-21-oic acid derivatives are frequently distinguished by a rapid onset of effectiveness, a high intensity of effectiveness, and a long period of activity. They show an advantageous resorbability and have a relatively good stability in galenic preparations.

Due to their antiinflammatory activity, the compounds of this invention are useful as topical antiinflammatory agents in human and veterinary medicine. These compounds are effective in localized treatment of skin diseases, e.g. contact dermatitis, eczema of a great variety of types, neurodermatoses, erythrodermia, burns, pruritus vulvae et ani, rosacea, erythematodes cutaneus, psoriasis, lichen ruber planus et verrucosus and similar skin diseases.

The compounds of this invention can be employed in mixture with conventional excipients, e.e., pharmaceutically acceptable organic or inorganic carrier substances suitable for parenteral, enteral or topical application which do not deleteriously react with the active compounds. Suitable pharmaceutically acceptable carriers include but are not limited to: water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g. lubricants, preservatives, stabilizers, wetting agents, emulsifiers, salts for influencing osmotic pressure, buffers, coloring, flavoring and/or aromatic substances and the like which do not deleteriously react with the active compounds. Sustained release compositions can be formulated including those wherein the active compound is protected with differently degradable coatings, e.g. by microencapsulation, multiple coatings, etc.

For parenteral application, particularly suitable are suppositories.

For topical application, these are employed as non-sprayable forms, viscous to semi-solid or solid forms comprising a carrier indigenous to topical applications and having a dynamic viscosity preferably greater than water. Suitable formulations include but are not limited to: solutions, suspensions, emulsions, creams, ointments, plasters, powders, liniments, salves, aerosols, etc., which are if desired sterilized or mixed with auxiliary agents, e.g. preservatives, stabilizers, wetting agents, buffers, salts for influencing osmotic pressure, etc. For topical application, also suitable are sprayable aerosol preparations wherein the active ingredient, preferably in combination with a solid or liquid inset carrier material, is packaged in a squeeze bottle or in admixture with a pressurized volatile, normally gaseous propellant, e.g. a freon. Usually, the active compounds of the invention are incorporated in lotion or ointment topical formulations in a concentration of about 0.001 to 1 weight percent.

The compounds of this invention are generally administered to animals, including but not limited to mammals, e.g. human beings, livestock, household pets, etc. An antiinflammatory effective daily dosage of the active compounds as administered topically to human beings generally comprises about 0.001 to 1.0, preferably 0.01 to 0.5 mg/cm$^2$. The dose can be administered singly or as divided dosages throughout the day.

Topical administration is preferred, the compounds of this invention being particularly valuable in the treatment of human beings afflicted with inflammatory skin disease. In this regard, they can be employed in substantially the same manner as the known compound fluocortolone.

It will be appreciated that the actual preferred amounts of active compounds used will vary according to the specific compound being utilized, the particular compositions formulated, the mode of application and the particular situs and organism being treated. Optimal application rates for a given set of conditions can be ascertained by those skilled in the art using conventional dosage determination tests in view of the above guidelines.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsuis; unless otherwise indicated, all parts and percentages are by weight. The values obtained in elemental analyses are within commonly accepted limits of error.

In Examples 16–36, portion (a), the solvent for the starting material is methanol.

EXAMPLE 1

(a) A solution of 2.2 g. of 14α,17α-ethylidenedioxy-21-hydroxy-4-pregnene-3,20-dione in 140 ml. of methanol is combined with 600 mg. of copper(II) acetate in 140 ml. of methanol. The reaction mixture is stirred for 1.5 hours while passing air therethrough. The mixture is then diluted with dichloromethane, washed with ammonium chloride and water, dried over sodium sulfate, and evaporated under vacuum. The yield is 2.4 g. of 14α,17α-ethylidenedioxy-3,20-dioxo-4-pregnen-21-al.

(b) One gram of the thus-obtained aldehyde is dissolved in 10 ml. of dichloromethane and 50 ml. of methanol. After adding 160 mg. of potassium cyanide, 1 ml. of glacial acetic acid, and 2 g. of manganese(IV) oxide, the solution is agitated for 30 minutes. The manganese(IV) oxide is filtered off, the filtrate is diluted with dichloromethane, washed with water, and dried and concentrated under vacuum. The residue is chromatographed on silica gel with a methylene chloride - acetone gradient (0–20% acetone). Yield: 230 mg. of the methyl ester of 14α,17α-ethylidenedioxy-3,20-dioxo-4-pregnene-21-oic acid; m.p. 156° C.

$[\alpha]_D^{25} = +150°$ (chloroform). UV: $\epsilon_{240} = 16,500$.

EXAMPLE 2

(a) A solution of 1.2 g. of 14α,17α-ethylidenedioxy-21-hydroxy-4-pregnene-3,20-dione is reacted, analogously to Example 1(a), to obtain 14α,17α-ethylidenedioxy-3,20-dioxo-4-pregnen-21-al.

(b) The thus-obtained aldehyde is reacted under the conditions described in Example 1(b), but with the use of ethanol. Yield: 400 mg. of the ethyl ester of 14α,17α-ethylidenedioxy-3,20-dioxo-4-pregnene-21-oic acid as a foam.

$[\alpha]_D^{25} = +132°$ (chloroform). UV: $\epsilon_{240} = 17,000$ (methanol).

EXAMPLE 3

(a) 14α,17α-Ethylidenedioxy-3,20-dioxo-4-pregnen-21-al is prepared corresponding to Example 1(a) from 14α,17α-ethylidenedioxy-21-hydroxy-4-pregnene-3,20-dione.

(b) One gram of the thus-obtained aldehyde is reacted under the conditions set forth in Example 1(b), but with the use of n-butanol. Yield: 600 mg. of the butyl ester of 14α,17α-ethylidenedioxy-3,20-dioxo-4-pregnene-21-oic acid as a foam.

$[\alpha]_D^{25} = +119°$ (chloroform). UV: $\epsilon_{237} = 18,000$ (methanol).

EXAMPLE 4

(a) A solution of 3.4 g. of 14α,17α-benzylidenedioxy-21-hydroxy-4-pregnene-3,20-dione is reacted analogously to Example 1(a) to 14α,17α-benzylidenedioxy-3,20-dioxo-4-pregnene-21-al. Yield: 3.8 g.

(b) 1.2 g. of the thus-obtained aldehyde is reacted, following the conditions of Example 1(b). Yield: 300 mg. of the methyl ester of 14α,17α-benzylidenedioxy-3,20-dioxo-4-pregnene-21-oic acid as a foam.

$[\alpha]_D^{25} = +89°$ (chloroform). UV: $\epsilon_{239} = 17,100$ (methanol).

EXAMPLE 5

(a) 14α,17α-Benzylidenedioxy-3,20-dioxo-4-pregnen-21-al is produced analogously to Example 4(a).

(b) 1.2 g. of the thus-obtained aldehyde is reacted under the conditions set forth in Example 1(b), but in ethanol. Yield: 300 mg. of the ethyl ester of 14α,17α-benzylidenedioxy-3,20-dioxo-4-pregnene-21-oic acid; m.p. 182° C.

$[\alpha]_D^{25} = +118°$ (chloroform). UV: $\epsilon_{240} = 16,900$ (methanol).

EXAMPLE 6

(a) 14α,17α-Benzylidenedioxy-3,20-dioxo-4-pregnen-21-al is prepared in accordance with Example 4(a).

(b) 1.5 g. of the thus-produced aldehyde is reacted under the conditions described in Example 1(b), but in n-butanol. Yield: 350 mg. of 14α,17α-benzylidenedioxy-3,20-dioxo-4-pregnene-21-oic acid butyl ester in the form of an oil.

$[\alpha]_D^{25} = +88°$ (chloroform). UV: $\epsilon_{237} = 16,200$ (methanol).

EXAMPLE 7

(a) A solution of 9 g. of 14α,17α-ethylidenedioxy-11α,21-dihydroxy-4-pregnene-3,20-dione is reacted analogously to Example 1(a) to 14α,17α-ethylidenedioxy-11α-hydroxy-3,20-dioxo-4-pregnen-21-al. Yield: 10 g.

(b) Five grams of the thus-obtained aldehyde is reacted under the conditions described in Example 1(b). Yield: 3.1 g. of the methyl ester of 14α,17α-ethylidenedioxy-11α-hydroxy-3,20-dioxo-4-pregnene-21-oic acid; m.p. 197° C.

$[\alpha]_D^{25} = +119°$ (chloroform). UV: $\epsilon_{241} = 16,600$ (methanol).

EXAMPLE 8

(a) 14α,17α-Ethylidenedioxy-11α-hydroxy-3,20-dioxo-4-pregnen-21-al is produced in correspondence with Example 7(a).

(b) 2.5 g. of the thus-produced aldehyde is reacted under the conditions disclosed in Example 1(b), but in ethanol. Yield: 900 mg. of the ethyl ester of 14α,17α-ethylidenedioxy-11α-hydroxy-3,20-dioxo-4-pregnene-21-oic acid; m.p. 162° C.

$[\alpha]_D^{25} = +108°$ (chloroform). UV: $\epsilon_{240} = 16,700$ (methanol).

EXAMPLE 9

(a) 14α,17α-Ethylidenedioxy-11α-hydroxy-3,20-dioxo-4-pregnen-21-al is produced analogously to Example 7(a).

(b) 2.5 g. of the thus-obtained aldehyde is reacted under the conditions described in Example 1(b), but using n-butanol. Yield: 900 mg. of the butyl ester of 14α,17α-ethylidenedioxy-11α-hydroxy-3,20-dioxo-4-pregnene-21-oic acid as an oil.

$[\alpha]_D = +95°$ (chloroform). UV: $\epsilon_{240} = 16,400$ (methanol).

EXAMPLE 10

A solution of 1.5 g. of the methyl ester of 14α,17α-ethylidenedioxy-11α-hydroxy-3,20-dioxo-4-pregnene-21-oic acid is added gradually dropwise to a solution, cooled to 0° C., of 4 g. of chromium trioxide in 100 ml. of methylene chloride and 7.2 ml. of pyridine. The mixture is then agitated for 80 hours at room temperature, filtered off, and the residue is extracted repeatedly with methylene chloride. The combined extracts are washed with water, dried over sodium sulfate, and evaporated under vacuum. The residue is chromatographed on silica gel with a methylene chloride - acetone gradient (0–20% acetone). Yield: 1.07 g. of the methyl ester of 14α,17α-ethylidenedioxy-3,11,20-trioxo-4-pregnene-21-oic acid; m.p. 241° C.

$[\alpha]_D^{25} = +195°$ (chloroform). UV: $\epsilon_{238} = 15,900$ (methanol).

EXAMPLE 11

500 mg. of the ethyl ester of 14α,17α-ethylidenedioxy-11α-hydroxy-3,20-dioxo-4-pregnene-21-oic acid is reacted in correspondence with Example 10 to obtain the ethyl ester of 14α,17α-ethylidenedioxy-3,11,20-trioxo-4-pregnene-21-oic acid. Yield: 365 mg., m.p. 190° C.

$[\alpha]_D^{25} = +184°$ (chloroform). UV: $\epsilon_{238} = 16,100$ (methanol).

EXAMPLE 12

500 mg. of the butyl ester of 14α,17α-ethylidenedioxy-11α-hydroxy-3,20-dioxo-4-pregnene-21-oic acid is reacted analogously to Example 10 to the butyl ester of 14α,17α-ethylidenedioxy-3,11,20-trioxo-4-pregnene-21-oic acid. Yield: 426 mg., m.p. 167° C.

$[\alpha]_D^{25} = +169°$ (chloroform). UV: $\epsilon_{237} = 16,100$ (methanol).

EXAMPLE 13

A solution of 370 mg. of the methyl ester of 14α,17α-ethylidenedioxy-3,20-dioxo-4-pregnene-21-oic acid in 10 ml. of dioxane is refluxed for 3 hours with 310 mg. of 2,3-dichloro-5,6-dicyano-p-benzoquinone. The 2,3-dichloro-5,6-dicyano-p-benzoquinone is filtered off, the filtrate is diluted with ether, washed with dilute sodium hydroxide solution and NaCl solution, dried, and concentrated. Preparative thin-layer chromatography in the system ether:chloroform = 8:2 yields 70 mg. of the methyl ester of 14α,17α-ethylidenedioxy-3,20-dioxo-1,4-pregnadiene-21-oic acid; m.p. 182° C.

$[\alpha]_D^{25} = +96°$ (chloroform). UV: $\epsilon_{243} = 14,500$ (methanol).

EXAMPLE 14

A solution of 2 g. of the methyl ester of 14α,17α-ethylidenedioxy-3,20-dioxo-4-pregnene-21-oic acid in 160 ml. of methanol and 100 ml. of methylene chloride is agitated under nitrogen with a solution of 1 g. of potassium hydroxide for one hour at room temperature. After diluting the solution with water, it is extracted 3 times with methylene chloride; the aqueous phase is acidified with semiconcentrated hydrochloric acid and again extracted with methylene chloride. The organic extracts are washed neutral, dried, and concentrated. Yield: 1.7 g. of 14α,17α-ethylidenedioxy-3,20-dioxo-4-pregnene-21-oic acid; m.p. 239° C. (under decomposition).

$[\alpha]_D^{25} = +126°$ (chloroform). UV: $\epsilon_{240} = 15,200$ (methanol).

EXAMPLE 15

A solution of 1 g. of 14α,17α-ethylidenedioxy-3,20-dioxo-4-pregnene-21-oic acid in 100 ml. of methanol is combined with 22.8 ml. of 0.1N sodium hydroxide solution until the transition point is reached of pH 7 (pH meter). The mixture is agitated for another 15 minutes and then concentrated. The residue is evaporated twice with ether. Yield: 900 mg. of the sodium salt of 14α,17α-ethylidenedioxy-3,20-dioxo-4-pregnene-21-oic acid; m.p. 260° C.

$[\alpha]_D^{25} = +114°$ (chloroform). UV: $\epsilon_{241} = 15,800$ (methanol).

EXAMPLE 16

(a) A solution of 900 mg. of 14α,17α-ethylidenedioxy-11β,21-dihydroxy-4-pregnene-3,20-dione is reacted in analogy to Example 1(a) to 14α,17α-ethylidenedioxy-11β-hydroxy-3,20-dioxo-4-pregnen-21-al.

(b) The thus-obtained aldehyde is reacted under the conditions described in Example 1(b). Yield: 310 mg. of the methyl ester of 14α,17α-ethylidenedioxy-11β-hydroxy-3,20-dioxo-4-pregnene-21-oic acid.

EXAMPLE 17

(a) A solution of 1.1 g. of 14α,17α-ethylidenedioxy-11β,21-dihydroxy-4-pregnene-3,20-dione is reacted analogously to Example 1(a) to 14α,17α-ethylidenedioxy-11β-hydroxy-3,20-dioxo-4-pregnen-21-al.

(b) The thus-produced aldehyde is reacted under the conditions set forth in Example 1(b), but with ethanol. Yield: 380 mg. of the ethyl ester of 14α,17α-ethylidenedioxy-11β-hydroxy-3,20-dioxo-4-pregnene-21-oic acid.

EXAMPLE 18

(a) A solution of 1.2 g. of 14α,17α-ethylidenedioxy-11β,21-dihydroxy-4-pregnene-3,20-dione is reacted in analogy to Example 1(a) to 14α,17α-ethylidenedioxy-11β-hydroxy-3,20-dioxo-4-pregnen-21-al.

(b) The thus-obtained aldehyde is reacted under the conditions indicated in Example 1(b), but with the use of n-butanol. Yield: 340 mg. of the butyl ester of 14α,17α-ethylidenedioxy-11β-hydroxy-3,20-dioxo-4-pregnene-21-oic acid.

EXAMPLE 19

(a) A solution of 1 g. of 14α,17α-ethylidenedioxy-9α-chloro-11β,21-dihydroxy-4-pregnene-3,20-dione yields, in analogy to Example 1(a), 14α,17α-ethylidenedioxy-9α-chloro-11β-hydroxy-3,20-dioxo-4-pregnen-21-al.

(b) The thus-produced aldehyde is reacted under the conditions set forth in Example 1(b). Yield: 400 mg. of the methyl ester of 14α,17α-ethylidenedioxy-9α-chloro-11β-hydroxy-3,20-dioxo-4-pregnene-21-oic acid.

EXAMPLE 20

(a) A solution of 1 g. of 14α,17α-ethylidenedioxy-9α-fluoro-11β,21-dihydroxy-4-pregnene-3,20-dione yields, analogously to Example 1(a), 14α,17α-ethylidenedioxy-9α-fluoro-11β-hydroxy-3,20-dioxo-4-pregnen-21-al.

(b) The thus-obtained aldehyde is reacted under the conditions disclosed in Example 1(b). Yield: 375 mg. of the methyl ester of 14α,17α-ethylidenedioxy-9α-fluoro-11β-hydroxy-3,20-dioxo-4-pregnene-21-oic acid.

EXAMPLE 21

(a) A solution of 1 g. of 14α,17α-ethylidenedioxy-9α-chloro-11β,21-dihydroxy-4-pregnene-3,20-dione is reacted analogously to Example 1(a) to 14α,17α-ethylidenedioxy-9α-chloro-11β-hydroxy-3,20-dioxo-4-pregnen-21-al.

(b) The thus-produced aldehyde is reacted under the conditions of Example 1(b), but with ethanol. Yield: 360 mg. of the ethyl ester of 14α,17α-ethylidenedioxy-9α-chloro-11β-hydroxy-3,20-dioxo-4-pregnene-21-oic acid.

EXAMPLE 22

(a) A solution of 1 g. of 14α,17α-ethylidenedioxy-9α-fluoro-11β,21-dihydroxy-4-pregnene-3,20-dione is reacted in analogy to Example 1(a) to obtain 14α,17α-ethylidenedioxy-9α-fluoro-11β-hydroxy-3,20-dioxo-4-pregnen-21-al.

(b) The resultant aldehyde is reacted under the conditions described in Example 1(b), but using ethanol. Yield: 352 mg. of the ethyl ester of 14α,17α-ethylidenedioxy-9α-fluoro-11β-hydroxy-3,20-dioxo-4-pregnene-21-oic acid.

EXAMPLE 23

(a) A solution of 1 g. of 14α,17α-ethylidenedioxy-9α-chloro-11β,21-dihydroxy-4-pregnene-3,20-dione is reacted in correspondence with Example 1(a) to 14α,17α-ethylidenedioxy-9α-chloro-11β-hydroxy-3,20-dioxo-4-pregnen-21-al.

(b) The thus-obtained aldehyde is reacted while observing the conditions of Example 1(b), but with n- butanol. Yield: 338 mg. of the butyl ester of 14α,17α-ethylidenedioxy-9α-chloro-11β-hydroxy-3,20-dioxo-4-pregnene-21-oic acid.

EXAMPLE 24

(a) A solution of 1 g. of 14α,17α-ethylidenedioxy-9α-fluoro-11β,21-dihydroxy-4-pregnene-3,20-dione is reacted analogously to Example 1(a) to 14α,17α-ethylidenedioxy-9α-fluoro-11β-hydroxy-3,20-dioxo-4-pregnen-21-al.

(b) The thus-obtained aldehyde is reacted under the conditions described in Example 1(b), but using n-butanol. Yield: 325 mg. of the butyl ester of 14α,17α-ethylidenedioxy-9α-fluoro-11β-hydroxy-3,20-dioxo-4-pregnene-21-oic acid.

EXAMPLE 25

(a) A solution of 1 g. of 14α,17α-ethylidenedioxy-9α,11β-dichloro-21-hydroxy-4-pregnene-3,20-dione is reacted in analogy to Example 1(a) to 14α,17α-ethylidenedioxy-9α,11β-dichloro-3,20-dioxo-4-pregnen-21-al.

(b) The thus-obtained aldehyde is reacted under the conditions described in Example 1(b). Yield: 410 mg. of the methyl ester of 14α,17α-ethylidenedioxy-9α,11β-dichloro-3,20-dioxo-4-pregnene-21-oic acid.

EXAMPLE 26

(a) A solution of 1 g. of 14α,17α-ethylidenedioxy-9α,11β-dichloro-21-hydroxy-4-pregnene-3,20-dione is reacted analogously to Example 1(a) to 14α,17α-ethylidenedioxy-9α,11β-dichloro-3,20-dioxo-4-pregnen-21-al.

(b) The thus-produced aldehyde is reacted under the conditions set forth in Example 1(b), but using ethanol. Yield: 390 mg. of the ethyl ester of 14α,17α-ethylidenedioxy-9α,11β-dichloro-3,20-dioxo-4-pregnene-21-oic acid.

EXAMPLE 27

(a) A solution of 1 g. of 14α,17α-ethylidenedioxy-9α,11β-dichloro-21-hydroxy-4-pregnene-3,20-dione is reacted in analogy to Example 1(a) to 14α,17α-ethylidenedioxy-9α,11β-dichloro-3,20-dioxo-4-pregnen-21-al.

(b) The thus-obtained aldehyde is reacted under the conditions described in Example 1(b), but with n-butanol. Yield: 335 mg. of the butyl ester of 14α,17α-ethylidenedioxy-9α,11β-dichloro-3,20-dioxo-4-pregnene-21-oic acid.

EXAMPLE 28

(a) A solution of 1 g. of 14α,17α-ethylidenedioxy-9α-chloro-11β-fluoro-21-hydroxy-4-pregnene-3,20-dione is reacted analogously to Example 1(a) to 14α,17α-ethylidenedioxy-9α-chloro-11β-fluoro-3,20-dioxo-4-pregnen-21-al.

(b) The resultant aldehyde is reacted under the conditions described in Example 1(b). Yield: 360 mg. of the methyl ester of 14α,17α-ethylidenedioxy-9α-chloro-11β-fluoro-3,20-dioxo-4-pregnene-21-oic acid.

EXAMPLE 29

(a) A solution of 1 g. of 14α,17α-ethylidenedioxy-9α-chloro-11β-fluoro-21-hydroxy-4-pregnene-3,20-dione is reacted in correspondence with Example 1(a) to 14α,17α-ethylidenedioxy-9α-chloro-11β-fluoro-3,20-dioxo-4-pregnen-21-al.

(b) The thus-obtained aldehyde is reacted under the conditions described in Example 1(b), but using ethanol. Yield: 340 mg. of the ethyl ester of 14α,17α-ethylidenedioxy-9α-chloro-11β-fluoro-3,20-dioxo-4-pregnene-21-oic acid.

EXAMPLE 30

(a) A solution of 1 g. of 14α,17α-ethylidenedioxy-9α-chloro-11β-fluoro-21-hydroxy-4-pregnene-3,20-dione is reacted analogously to Example 1(a) to 14α,17α-ethylidenedioxy-9α-chloro-11β-fluoro-3,20-dioxo-4-pregnen-21-al.

(b) The thus-produced aldehyde is reacted under the conditions set forth in Example 1(b), but with the use of n-butanol. Yield: 295 mg. of the butyl ester of 14α,17α-ethylidenedioxy-9α-chloro-11β-fluoro-3,20-dioxo-4-pregnene-21-oic acid.

EXAMPLE 31

(a) A solution of 1 g. of 14α,17α-ethylidenedioxy-11β-fluoro-21-hydroxy-4-pregnene-3,20-dione is reacted in analogy to Example 1(a) to 14α,17α-ethylidenedioxy-11β-fluoro-3,20-dioxo-4-pregnen-21-al.

(b) The thus-obtained aldehyde is reacted under the conditions of Example 1(b). Yield: 370 mg. of the methyl ester of 14α,17α-ethylidenedioxy-11β-fluoro-3,20-dioxo-4-pregnene-21-oic acid.

EXAMPLE 32

(a) A solution of 1 g. of 14α,17α-ethylidenedioxy-11β-fluoro-21-hydroxy-4-pregnene-3,20-dione is reacted analogously to Example 1(a) to 14α,17α-ethylidenedioxy-11β-fluoro-3,20-dioxo-4-pregnen-21-al.

(b) The thus-produced aldehyde is reacted under the conditions set out in Example 1(b), but with the use of ethanol. Yield: 355 mg. of the ethyl ester of 14α,17α-ethylidenedioxy-11β-fluoro-3,20-dioxo-4-pregnene-21-oic acid.

EXAMPLE 33

(a) A solution of 1 g. of 14α,17α-ethylidenedioxy-11β-fluoro-21-hydroxy-4-pregnene-3,20-dione is reacted in analogy to Example 1(a) to 14α,17α-ethylidenedioxy-11β-fluoro-3,20-dioxo-4-pregnen-21-al.

(b) The resultant aldehyde is reacted under the conditions of Example 1(b), but with n-butanol. Yield: 305 mg. of the butyl ester of 14α,17α-ethylidenedioxy-11β-fluoro-3,20-dioxo-4-pregnene-21-oic acid.

EXAMPLE 34

A solution of 400 mg. of the butyl ester of 14α,17α-ethylidenedioxy-3,11,20-trioxo-4-pregnene-21-oic acid is reacted analogously to Example 13. Yield: 95 mg. of the butyl ester of 14α,17α-ethylidenedioxy-3,11,20-trioxo-1,4-pregnadiene-21-oic acid.

EXAMPLE 35

A solution of 1 g. of the methyl ester of 14α,17α-ethylidenedioxy-3,11,20-trioxo-4-pregnene-21-oic acid is reacted analogously to Example 14. Yield: 810 mg. of 14α,17α-ethylidenedioxy-3,11,20-trioxo-4-pregnene-21-oic acid.

EXAMPLE 36

A solution of 400 mg. of 14α,17α-ethylidenedioxy-3,11,20-trioxo-4-pregnene-21-oic acid is reacted analogously to Example 15. Yield: 320 mg. of the sodium salt of 14α,17α-ethylidenedioxy-3,11,20-trioxo-4-pregnene-21-oic acid as an amorphous product.

The following example serves to illustrate the preparation and use of pharmaceutical compositions containing antiinflammatory amounts of the compositions according to Formula I adapted for topical application:

Ointment Composition:

0.1% Butylester of 14α,17α-ethylidenedioxy-11β-hydroxy-3,20-dioxo-4-pregnene-21-oic acid
2.50% "Allercur" hexachlorophenate, micronized, particle size about 8 μ ("Allercur"=registered trademark for 1-(p-chlorobenzyl)-2-pyrrolidylmethylenebenzimidazole)
6.00% "Hostaphat KW 340" (tertiary ester of o-phosphoric acid and wax alcohol tetraglycol ether)
0.10% Sorbic acid
10.00% Neutral oil ("Migloyol 812")
3.50% Stearyl alcohol
1.50% Lanolin, anhydrous DAB (German Pharmacopeia) 6
76.39% Desalted water The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Pregnane-21-oic acid derivatives of the formula

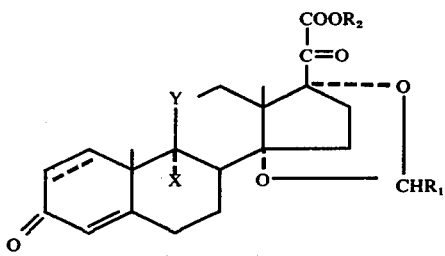

wherein
the linkage ===== represents a single bond or a double bond;
X is hydrogen, fluorine or chlorine;
Y is methylene, hydroxymethylene, alkanoyloxymethylene, carbonyl, fluoromethylene or chloromethylene;
$R_1$ is hydrogen, alkyl of 1–6 carbon atoms, phenyl or naphthyl substituted with 0–3 lower alkyl, lower alkoxy or chlorine; and
$R_2$ represents a hydrogen atom, the carboxylic acid salt cation of a physiologically compatible base or the residue of a physiologically acceptable aliphatic or cycloaliphatic alcohol of 1–18 carbon atoms optionally substituted by a member selected from the group consisting of lower alkyl, cyclopentyl, cyclohexyl, hydroxy, lower alkoxy, free or esterified carboxyl and the sodium and potassium salts thereof, amino, mono- or di-lower alkylamino and the hydrochloride, hydrobromide, sulfate, phosphate, oxalate, maleate or tartrate salts thereof.

2. A compound according to claim 1 wherein X is hydrogen and Y is methylene, α- or β-hydroxymethylene, carbonyl or β-fluoromethylene.

3. A compound according to claim 1 wherein X is fluorine and Y is β-hydroxymethylene or carbonyl.

4. A compound according to claim 1 wherein X is chlorine and Y is β-hydroxymethylene, carbonyl, a β-fluoromethylene group or a β-chloromethylene group.

5. A compound according to claim 1 selected from the group consisting of 14α,17α-ethylidenedioxy-3,20-dioxo-4-pregnene-21-oic acid methyl ester; 14α,17α-ethylidenedioxy-3,20-dioxo-4-pregnene-21-oic acid ethyl ester; 14α,17α-ethylidenedioxy-3,20-dioxo-4-pregnene-21-oic acid butyl ester; 14α,17α-ethylidenedioxy-3,20-dioxo-1,4-pregnadiene-21-oic acid methyl ester; 14α,17α-ethylidenedioxy-3,20-dioxo-4-pregnene-21-oic acid; and the sodium salt of 14α,17α-ethylidenedioxy-3,20-dioxo-4-pregnene-21-oic acid.

6. A compound according to claim 1 selected from the group consisting of 14α,17α-benzylidenedioxy-3,20-dioxo-4-pregnene-21-oic acid methyl ester; 14α,17α-benzylidenedioxy-3,20-dioxo-4-pregnene-21-oic acid ethyl ester; and 14α,17α-benzylidenedioxy-3,20-dioxo-4-pregnene-21-oic acid butyl ester.

7. A compound according to claim 1 selected from the group consisting of 14α,17α-ethylidenedioxy-11α-hydroxy-3,20-dioxo-4-pregnene-21-oic acid methyl ester; 14α,17α-ethylidenedioxy-11α-hydroxy-3,20-dioxo-4-pregnene-21-oic acid ethyl ester; 14α,17α-ethylidenedioxy-11α-hydroxy-3,20-dioxo-4-pregnene-21-oic acid butyl ester; 14α,17α-ethylidenedioxy-11β-hydroxy-3,20-dioxo-4-pregnene-21-oic acid methyl ester; 14α,17α-ethylidenedioxy-11β-hydroxy-3,20-dioxo-4-pregnene-21-oic acid ethyl ester; and 14α,17α-ethylidenedioxy-11β-hydroxy-3,20-dioxo-4-pregnene-21-oic acid butyl ester.

8. A compound according to claim 1 selected from the group consisting of 14α,17α-ethylidenedioxy-3,11,20-trioxo-4-pregnene-21-oic acid methyl ester; 14α,17α-ethylidenedioxy-3,11,20-trioxo-4-pregnene-21-oic acid ethyl ester; 14α,17α-ethylidenedioxy-3,11,20-trioxo-4-pregnene-21-oic acid butyl ester; 14α,17α-ethylidenedioxy-3,11,20-trioxo-1,4-pregnadiene-21-oic acid butyl ester; 14α,17α-ethylidenedioxy-3,11,20-trioxo-4-pregnene-21-oic acid; and the sodium salt of 14α,17α-ethylidenedioxy-3,11,20-trioxo-4-pregnene-21-oic acid.

9. A compound according to claim 1 selected from the group consisting of 14α,17α-ethylidenedioxy-9α-chloro-11β-hydroxy-3,20-dioxo-4-pregnene-21-oic acid methyl ester; 14α,17α-ethylidenedioxy-9α-fluoro-11β-hydroxy-3,20-dioxo-4-pregnene-21-oic acid methyl ester; 14α,17α-ethylidenedioxy-9α-chloro-11β-hydroxy-3,20-dioxo-4-pregnene-21-oic acid ethyl ester; 14α,17α-ethylidenedioxy-9α-fluoro-11β-hydroxy-3,20-dioxo-4-pregnene-21-oic acid ethyl ester; 14α,17α-ethylidenedioxy-9α-chloro-11β-hydroxy-3,20-dioxo-4-pregnene-21-oic acid butyl ester; 14α,17α-ethylidenedioxy-9α-fluoro-11β-hydroxy-3,20-dioxo-4-pregnene-21-oic acid butyl ester; and 14α,17α-ethylidenedioxy-9α-chloro-11β-hydroxy-3,20-dioxo-1,4-pregnadiene-21-oic acid ethyl ester.

10. A compound according to claim 1 selected from the group consisting of 14α,17α-ethylidenedioxy-9α,11β-dichloro-3,20-dioxo-4-pregnene-21-oic acid methyl ester; 14α,17α-ethylidenedioxy-9α,11β-dichloro-3,20-dioxo-4-pregnene-21-oic acid ethyl ester; 14α,17α-ethylidenedioxy-9α,11β-dichloro-3,20-dioxo-4-pregnene-21-oic acid butyl ester; 14α,17α-ethylidenedioxy-9α-chloro-11β-fluoro-3,20-dioxo-4-pregnene-21-oic acid methyl ester; 14α,17α-ethylidenedioxy-9α-chloro-11β-fluoro-3,20-dioxo-4-pregnene-21-oic acid ethyl ester; and 14α,17α-ethylidenedioxy-9α-chloro-11β-fluoro-3,20-dioxo-4-pregnene-21-oic acid butyl ester.

11. A compound according to claim 1 selected from the group consisting of 14α,17α-ethylidenedioxy-11β-fluoro-3,20-dioxo-4-pregnene-21-oic acid methyl ester; 14α,17α-ethylidenedioxy-11β-fluoro-3,20-dioxo-4-pregnene-21-oic acid ethyl ester; and 14α,17α-ethylidenedioxy-11β-fluoro-3,20-dioxo-4-pregnene-21-oic acid butyl ester.

12. A pharmaceutical composition comprising an antiinflammatory amount and concentration of a compound according to claim 1 in combination with a physiologically acceptable carrier adapted for topical application.

13. A method for reducing inflammation of the skin which comprises topically applying an antiinflammatory amount of a composition according to claim 12 onto the skin of an animal afflicted with inflamed tissue at the situs thereof to reduce said inflammation.

14. A compound according to claim 1, wherein $R_1$ is alkyl of 1-6 carbon atoms.

15. A compound according to claim 1, wherein $R_1$ is phenyl or naphthyl substituted by 0-3 of lower alkyl, lower alkoxy or halogen.

16. A compound according to claim 1, wherein $R_1$ is phenyl or naphthyl substituted by 0-1 of methyl, methoxy, fluorine or chlorine.

17. A compound according to claim 1, wherein $R_2$ is alkyl of 1-6 carbon atoms.

18. A compound according to claim 1, wherein $R_2$ is a cycloaliphatic or aromatic ring having 5 or 6 ring carbon atoms.

19. A compound according to claim 1, wherein $R_2$ is hydrogen.

20. A compound according to claim 1, wherein $R_2$ is sodium.

* * * * *